US008446332B2

(12) United States Patent
Homan

(10) Patent No.: US 8,446,332 B2
(45) Date of Patent: May 21, 2013

(54) ANTENNA APPARATUS

(75) Inventor: Masatoshi Homan, Hino (JP)

(73) Assignee: Olympus Medical Systems Corp., Tokyo (JP)

(*) Notice: Subject to any disclaimer, the term of this patent is extended or adjusted under 35 U.S.C. 154(b) by 0 days.

(21) Appl. No.: 13/540,761

(22) Filed: Jul. 3, 2012

(65) Prior Publication Data
US 2013/0027267 A1   Jan. 31, 2013

Related U.S. Application Data

(63) Continuation of application No. PCT/JP2011/074354, filed on Oct. 21, 2011.

(30) Foreign Application Priority Data

Nov. 29, 2010   (JP) .................................. 2010-265757

(51) Int. Cl.
H01Q 21/00   (2006.01)
(52) U.S. Cl.
USPC ............ 343/810; 343/893; 343/879; 343/718
(58) Field of Classification Search
USPC ................. 343/718, 793, 799, 810, 879, 893
See application file for complete search history.

(56) References Cited

U.S. PATENT DOCUMENTS

| | | | | |
|---|---|---|---|---|
| 3,329,954 | A * | 7/1967 | Travers | 342/445 |
| 8,217,849 | B2 * | 7/2012 | Sardariani et al. | 343/793 |
| 2006/0264734 | A1 | 11/2006 | Kimoto et al. | |
| 2007/0188401 | A1 | 8/2007 | Kubokawa et al. | |
| 2007/0270628 | A1 | 11/2007 | Kawano et al. | |
| 2009/0312604 | A1 | 12/2009 | Kimoto et al. | |
| 2010/0280340 | A1 | 11/2010 | Homan et al. | |

FOREIGN PATENT DOCUMENTS

| | | |
|---|---|---|
| JP | 2003-608 A | 1/2003 |
| JP | 2005-218502 A | 8/2005 |
| JP | 2005-252727 A | 9/2005 |
| JP | 2006-296 A | 1/2006 |
| JP | 2006-68501 A | 3/2006 |
| JP | 2006-280829 A | 10/2006 |
| JP | 2007-75154 A | 3/2007 |
| WO | WO 2010-044389 A1 | 4/2010 |

OTHER PUBLICATIONS

Decision of a Patent Grant dated Sep. 11, 2012 issued in related Japanese Patent Application No. 2012-530043.
International Search Report PCT/JP2011/074354 dated Dec. 13, 2011.

* cited by examiner

Primary Examiner — Dieu H Duong
(74) Attorney, Agent, or Firm — Scully, Scott, Murphy & Presser, P.C.

(57) ABSTRACT

An antenna apparatus includes: first and second receiving antennas disposed on a plane at equal distances from a reference point and face each other with the reference point therebetween; third and fourth receiving antennas disposed on the plane, a gravity center of the third and fourth receiving antennas being an equal distance from the reference point, a straight line connecting the gravity centers of the third and fourth receiving antennas is at 90 degrees with respect to a straight line connecting gravity centers of the first and second receiving antennas; fifth, sixth, seventh and eighth receiving antennas disposed on the plane, having gravity centers on straight lines different from each other and rotated by an angle of 45 degrees from the straight line connecting the gravity centers of the first and second receiving antennas and the straight line connecting the gravity centers of the third and fourth receiving antennas, respectively.

10 Claims, 9 Drawing Sheets

ANTENNA APPARATUS

CROSS REFERENCES TO RELATED APPLICATIONS

This application is a continuation of PCT international application Ser. No. PCT/JP2011/074354 filed on Oct. 21, 2011 which designates the United States, incorporated herein by reference, and which claims the benefit of priority from Japanese Patent Applications No. 2010-265757, filed on Nov. 29, 2010, incorporated herein by reference.

BACKGROUND OF THE INVENTION

1. Field of the Invention

The present invention relates to a receiving antenna apparatus that receives a radio signal transmitted from a capsule endoscope inside of a subject.

2. Description of the Related Art

Conventionally, in the field of an endoscope, a capsule endoscope with a built-in imaging function and a radio communication function, which are provided in a capsule-shaped casing formed to a size that can be introduced into the gut of a subject such as a patient, is known. The capsule endoscope is first swallowed from the mouth of the subject and then it moves in the inside of the subject such as the gut by peristaltic movement and the like. Then, it sequentially captures images of the inside of the subject to generate image data, and sequentially transmits the image data.

The image data thus transmitted from the capsule endoscope by wireless transmission is received by a receiving apparatus through a receiving antenna provided outside the subject. The receiving apparatus stores the image data received through the receiving antenna in a built-in memory.

The subject can freely act during a period until the capsule endoscope is excreted after the capsule endoscope is swallowed, by carrying the receiving apparatus that has a radio communication function and a memory function. After the examination, a practitioner such as a doctor puts the image data accumulated in the memory of the receiving apparatus in an image display apparatus so that images of the inside of the subject which correspond to the images obtained by the capsule endoscope, that is, the internal organs' images are displayed on a display of the image display apparatus. The practitioner observes the images of the internal organs and the like displayed on the display, and diagnoses the subject.

In receiving the radio signal transmitted from the capsule endoscope, a typical receiving apparatus has a plurality of receiving antennas arranged in a dispersed manner outside the subject, selects one antenna with the strongest received strength, and receives the radio signal by the selected antenna. For example, there is a known receiving apparatus in which reception switching among a plurality of antennas placed outside a subject is performed and which detects the position of a capsule endoscope in the subject that is the source of a radio signal based on the field strength received by each antenna (See Japanese Patent Application Laid-open Publication No. 2003-000608).

SUMMARY OF THE INVENTION

An antenna apparatus according to an aspect of the present invention includes: a first receiving antenna and a second receiving antenna respectively disposed at positions on a plane which are in an equal distance from a reference point and face each other with the reference point therebetween; a third receiving antenna and a fourth receiving antenna disposed at positions on the plane, a gravity center of the third receiving antenna and a gravity center of the fourth receiving antenna being in an equal distance from the reference point on the plane, a straight line connecting the gravity centers of the third receiving antenna and the fourth receiving antenna being at an angle of 90 degrees with respect to a straight line connecting a gravity center of the first receiving antenna and a gravity center of the second receiving antenna; a fifth receiving antenna, a sixth receiving antenna, a seventh receiving antenna, and an eighth receiving antenna disposed respectively at positions on the plane, gravity centers of the fifth to eighth receiving antennas being on straight lines different from each other, which are rotated by an angle of 45 degrees from the straight line connecting the gravity centers of the first receiving antenna and the second receiving antenna and the straight line connecting the gravity centers of the third receiving antenna and the gravity center of the fourth receiving antenna, respectively, wherein each of the first to the eighth receiving antennas is formed such that two conductive wires symmetrically extend to left and right sides to be in a straight line and have a same length, a direction of the conductive wires of the first receiving antenna is parallel to a direction of the conductive wires of the second receiving antenna, a direction of the conductive wires of the third receiving antenna is parallel to a direction of the conductive wires of the fourth receiving antenna and orthogonal to the direction of the conductive wires of the first receiving antenna and the direction of the conductive wires of the second receiving antenna, a direction of the conductive wires of the fifth receiving antenna is parallel to a direction of the conductive wires of the sixth receiving antenna, and a direction of the conductive wires of the seventh receiving antenna is parallel to a direction of the conductive wires of the eighth receiving antenna and orthogonal to the direction of the conductive wires of the fifth receiving antenna and the direction of the conductive wires of the sixth receiving antenna.

The above and other features, advantages and technical and industrial significance of this invention will be better understood by reading the following detailed description of presently preferred embodiments of the invention, when considered in connection with the accompanying drawings.

DETAILED DESCRIPTION OF THE PREFERRED EMBODIMENTS

Figure 1:
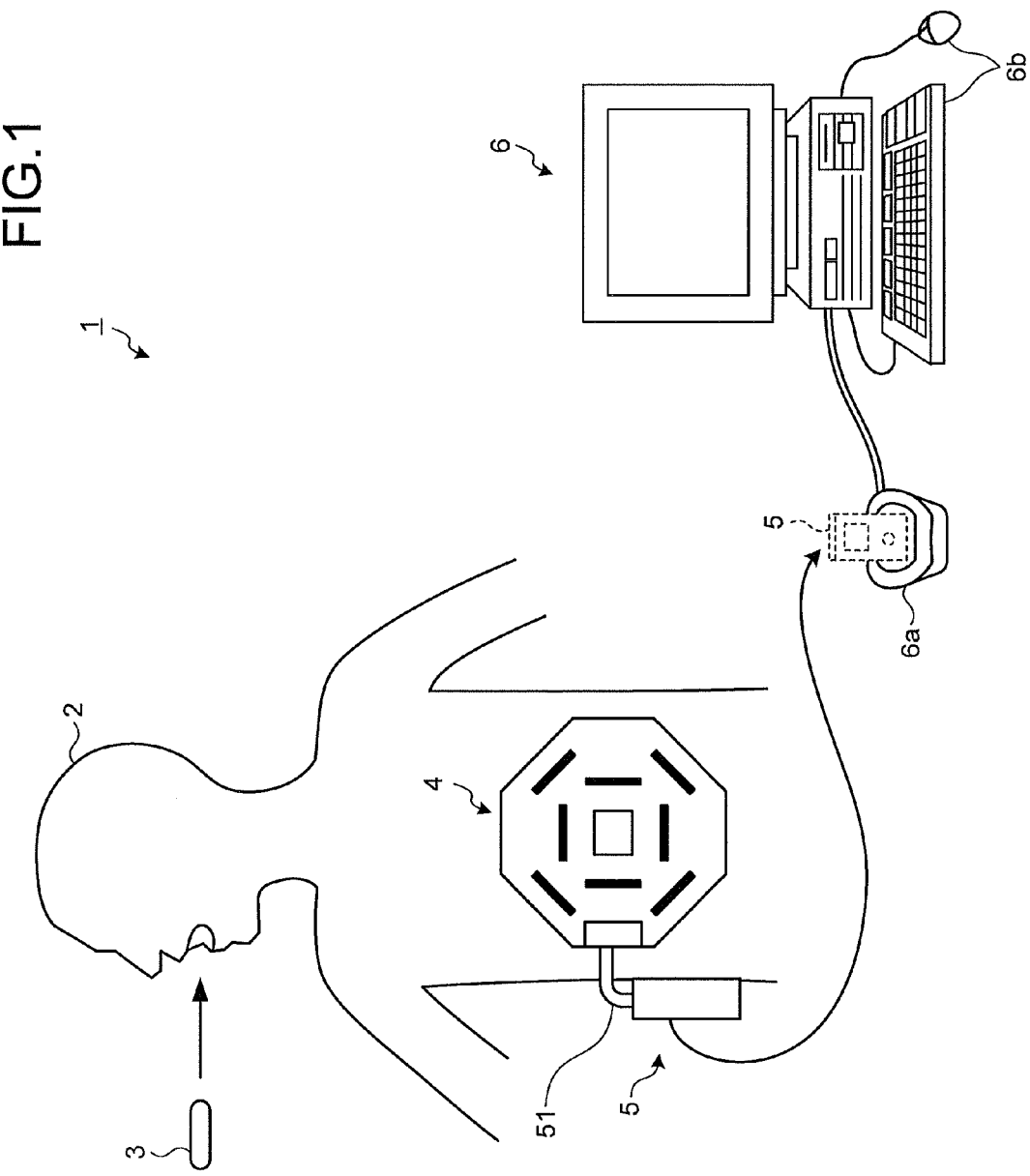
FIG. 1 is a schematic diagram that illustrates an outline of a configuration of a capsule endoscope system provided with an antenna apparatus according to an embodiment of the present invention.

Hereinbelow, an antenna apparatus according to an embodiment of the present invention is described referring to the drawings. In the following description, a capsule endoscope system including a capsule endoscope, which is introduced into the inside of a subject to capture in-vivo images of the subject, is presented as an example of an antenna apparatus according the present invention. However, the present invention is not limited by this embodiment.

As illustrated in FIG. 1, a capsule endoscope system 1 includes a capsule endoscope 3 that captures an in-vivo image of a subject 2, an antenna apparatus 4 that receives a radio signal transmitted from the capsule endoscope 3 introduced in the subject 2, a receiving apparatus 5 that performs predetermined processing on the radio signal input from the antenna apparatus 4 and stores the processing result, and an image display apparatus 6 that displays an image corresponding to image data of the inside of the subject 2 captured by the capsule endoscope 3.

The capsule endoscope 3 has an imaging function to capture an image of the inside of the subject 2, and a radio communication function to transmit image data obtained by capturing an image of the inside of the subject 2 to the receiving apparatus 5. The capsule endoscope 3 is swallowed by the subject 2 so that it passes through the esophagus of the subject 2 and moves in the body cavity of the subject by peristaltic movement of the lumen of the gut. The capsule endoscope 3 sequentially captures images of the body cavity of the subject 2 at intervals of a minute time, for example, an interval of 0.5 seconds while moving in the body cavity, and sequentially generates and transmits image data of the captured images of the inside of the subject 2 to the receiving apparatus 5. In this case, the capsule endoscope 3 generates a transmission signal, which includes the image data and received-field-strength detection data including position information (beacon) etc. which makes received field strength easy to be detected, and transmits a radio signal obtained by modulating the generated transmission signal to the receiving apparatus 5 by wireless transmission.

The antenna apparatus 4 outputs the radio signal, received from the capsule endoscope 3, to the receiving apparatus 5 through an antenna cable 51. The antenna apparatus 4 is fixed to the subject 2 with a belt or the like during the examination.

The receiving apparatus 5 acquires the radio signal, which is transmitted from the capsule endoscope 3 by wireless transmission, through the antenna apparatus 4 and the antenna cable 51. The receiving apparatus 5 acquires the image data of the inside of the subject 2 based on the radio signal received from the capsule endoscope 3. The receiving apparatus 5 stores received-field-strength information and time information which indicates a time point in association with the received image data. The receiving apparatus 5 is carried by the subject 2 while the capsule endoscope 3 is capturing images, that is, during a period from when the endoscope is introduced from the mount of the subject 2 and to when the endoscope passes through the gut and is finally excreted out of the subject 2. After the examination using the capsule endoscope 3 ends, the receiving apparatus 5 is removed from the subject 2 and is then connected to the image display apparatus 6 so that information on the image, data etc. received from the capsule endoscope 3 can be transmitted.

The image display apparatus 6 is configured by a work station or a personal computer including a display such as a liquid crystal display. The image display apparatus 6 displays an image corresponding to the image data in the subject 2 acquired by the receiving apparatus 5. A cradle 6a that reads the image data from the memory of the receiving apparatus 5 and an operation input devices 6b such as a keyboard and a mouse are connected to the image display apparatus 6. The cradle 6a acquires image data, the received-field-strength information associated with the image data, time information, and relevant information such as identification information of the capsule endoscope 3, from the memory of the receiving apparatus 5 when the receiving apparatus 5 is mounted, and transmits the acquired various information to the image display apparatus 6. The operation input device 6b accepts the input from the user. As a result, the user observes living body parts in the subject 2, for example, the esophagus, the stomach, the small intestine, and the large intestine, and makes a diagnosis on the subject 2 while operating the operation input device 6b and viewing the images of the inside of the subject 2 which are sequentially displayed by the image display apparatus 6.

Figure 2:
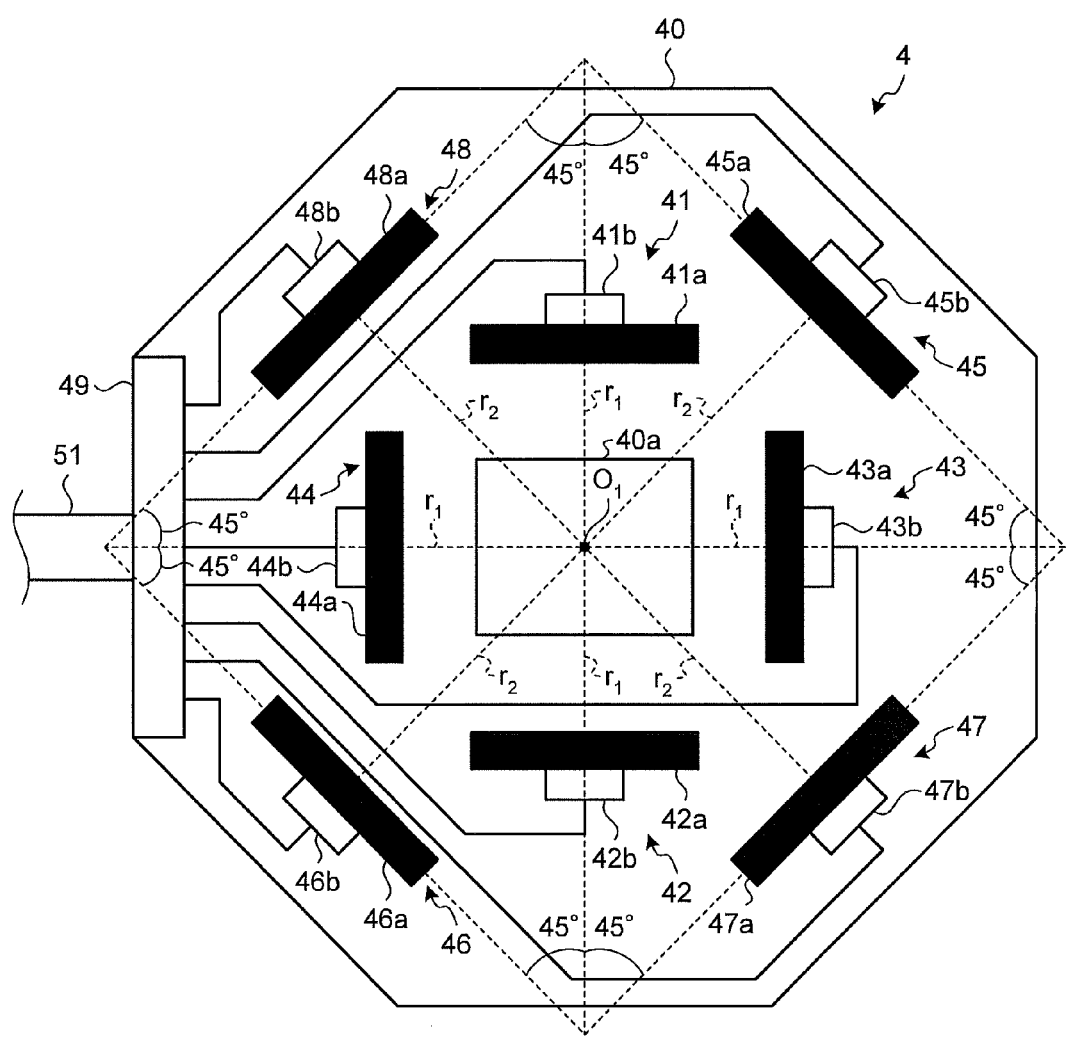
FIG. 2 is a plan view that illustrates a schematic configuration of the antenna apparatus according to the embodiment of the present invention.

Next, details of a configuration of the antenna apparatus 4 illustrated in FIG. 2 are described. FIG. 2 is a plan view that illustrates a schematic configuration of the antenna apparatus 4. As illustrated in FIG. 2, the antenna apparatus 4 includes a plate unit 40, a first receiving antenna 41, a second receiving antenna 42, a third receiving antenna 43, a fourth receiving antenna 44, a fifth receiving antenna 45, a sixth receiving antenna 46, a seventh receiving antenna 47, an eighth receiving antenna 48, and a connector 49. The first to eighth receiving antennas 41 to 48 are provided on one plate unit 40.

The plate unit 40 is formed of a sheet-like flexible substrate. The principal surface of the plate unit 40 is substantially octagonal. The plate unit 40 is formed to a size that can cover the entire surface of the abdomen of the subject 2, for example, 200 mm in length×200 mm in width. The plate unit 40 has an opening 40a. The opening 40a is formed such that the center is coincident with a reference point $O_1$ of the plate unit 40. The opening 40a functions as a positioning unit which positions the antenna apparatus with respect to the subject 2 when the antenna apparatus is attached to the subject 2. As a result, when the plate unit 40 is attached to the subject 2, the antenna apparatus 4 can be easily positioned. The opening 40a may be formed using a transparent member, for example, a transparent vinyl sheet, etc. Incidentally, the principal surface of the plate unit 40 does not necessarily have a substantial octagonal shape, but may have a rectangular shape, etc.

The first receiving antenna 41 and the second receiving antenna 42 are disposed at positions which face each another with the reference point $O_1$ therebetween. The first receiving antenna 41 and the second receiving antenna 42 are disposed at positions which are in an equal distance from the reference point $O_1$. Specifically, the first receiving antenna 41 and the second receiving antenna 42 are disposed respectively at the positions on the plate unit 40 which are in a distance of $r_1$ from the reference point $O_1$. As for the first receiving antenna 41 and the second receiving antenna 42, an element 41a and an element 42a thereof are formed on the plate unit 40 as printed circuits. The first receiving antenna 41 and the second receiving antenna 42 include an active circuit 41b and an active circuit 42b connected to the element 41a and the element 42a, respectively. The active circuits 41b and 42b are both formed on the plate unit 40 as planar circuits, respectively. The active circuits 41b and 42b perform impedance matching respectively for the first receiving antenna 41 and the second receiving antenna 42, performs amplification processing including amplification and attenuation on a received radio signal, and performs balanced-to-unbalanced transformation on the received radio signal. The first receiving antenna 41 and the second receiving antenna 42 are connected to the connector 49 provided in the plate unit 40 via planar transmission lines (striplines), respectively.

The third receiving antenna 43 and the fourth receiving antenna 44 are disposed at positions which are in-plane rotated about the reference point $O_1$ by 90 degrees respectively from the first receiving antenna 41 and the second receiving antenna 42. The third receiving antenna 43 and the fourth receiving antenna 44 are disposed respectively at positions on the plate unit 40 which are in a distance of $r_1$ from the reference point $O_1$. As for the third receiving antenna 43 and the fourth receiving antenna 44, an element 43a and an element 44a thereof are both formed on the plate unit 40 as printed circuits. The third receiving antenna 43 and the fourth receiving antenna 44 include an active circuit 43b and an active circuit 44b connected to the element 43a and the element 44a, respectively. The third receiving antenna 43 and the fourth receiving antenna 44 are connected to the connector 49 via planar transmission lines, respectively.

The fifth receiving antenna 45 and the sixth receiving antenna 46 are disposed at positions which are in-plane rotated about the reference point $O_1$ by 45 degrees respectively from the first receiving antenna 41 and the second receiving antenna 42. The fifth receiving antenna 45 and the sixth receiving antenna 46 are disposed to be closer to outer peripheries of the plane than the first receiving antenna 41 and the second receiving antenna 42 within the plane. Specifically, the fifth receiving antenna 45 and the sixth receiving antenna 46 are disposed respectively at positions on the plate unit 40 which are each in a distance of $r_2$ ($r_1<r_2$) from the reference point $O_1$. As for the fifth receiving antenna 45 and the sixth receiving antenna 46, an element 45a and an element 46a thereof are both formed on the plate unit 40 as printed circuits. The fifth receiving antenna 45 and the sixth receiving antenna 46 include an active circuit 45b and an active circuit 46b connected to the element 45a and the element 46a, respectively. The fifth receiving antenna 45 and the sixth receiving antenna 46 are connected to the connector 49 via planar transmission lines, respectively.

The seventh receiving antenna 47 and the eighth receiving antenna 48 are disposed at positions which are in-plane rotated about the reference point $O_1$ by 90 degrees respectively from the fifth receiving antenna 45 and the sixth receiving antenna 46. The seventh receiving antenna 47 and the eighth receiving antenna 48 are disposed to be closer to outer peripheries of the plane than the first receiving antenna 41 and the second receiving antenna 42 within the plane. Specifically, the seventh receiving antenna 47 and the eighth receiving antenna 48 are disposed respectively at positions on the plate unit 40 which are each in a distance of $r_2$ ($r_1<r_2$) from the reference point $O_1$. As for the seventh receiving antenna 47 and the eighth receiving antenna 48, an element 47a and an element 48a thereof are both formed on the plate unit 40 as printed circuits. The seventh receiving antenna 47 and the eighth receiving antenna 48 include an active circuit 47b and an active circuit 48b connected to the element 47a and the element 48a, respectively. The seventh receiving antenna 47 and the eighth receiving antenna 48 are connected to the connector 49 via planar transmission lines, respectively.

Figure 3:
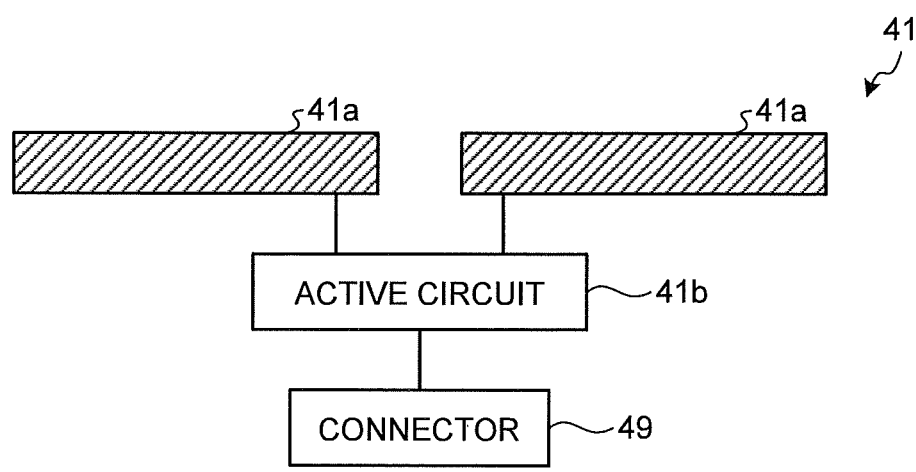
FIG. 3 is a block diagram that illustrates a schematic configuration of a first receiving antenna illustrated in FIG. 2.

Here, details of the configuration of the first receiving antenna 41 illustrated in FIG. 2 are described. FIG. 3 is a block diagram that illustrates the configuration of the first receiving antenna.

As illustrated in FIG. 3, the first receiving antenna 41 is configured by a balanced antenna. Specifically, the first receiving antenna 41 is configured such that the element 41a is a dipole antenna having two linear conductive wires. In the first receiving antenna 41, the two linear conductive wires of the element 41a are in a straight line, symmetrically extend to left and right sides, and have the same length. Because of this configuration, the first receiving antenna 41 exhibits large loss in cross polarization compared with main polarization. Since the second to eighth receiving antennas 42 to 48 which are described above have the same configuration as the first receiving antenna 41, the description thereof is not repeated. In the present embodiment, the number of receiving antennas is not necessarily construed to be limited to 8, but may be more than 8.

With the configuration described above, the antenna apparatus 4 can receive all polarizations transmitted by the capsule endoscope 3 regardless of the orientation and position of the capsule endoscope 3 in the subject 2.

Figure 4:
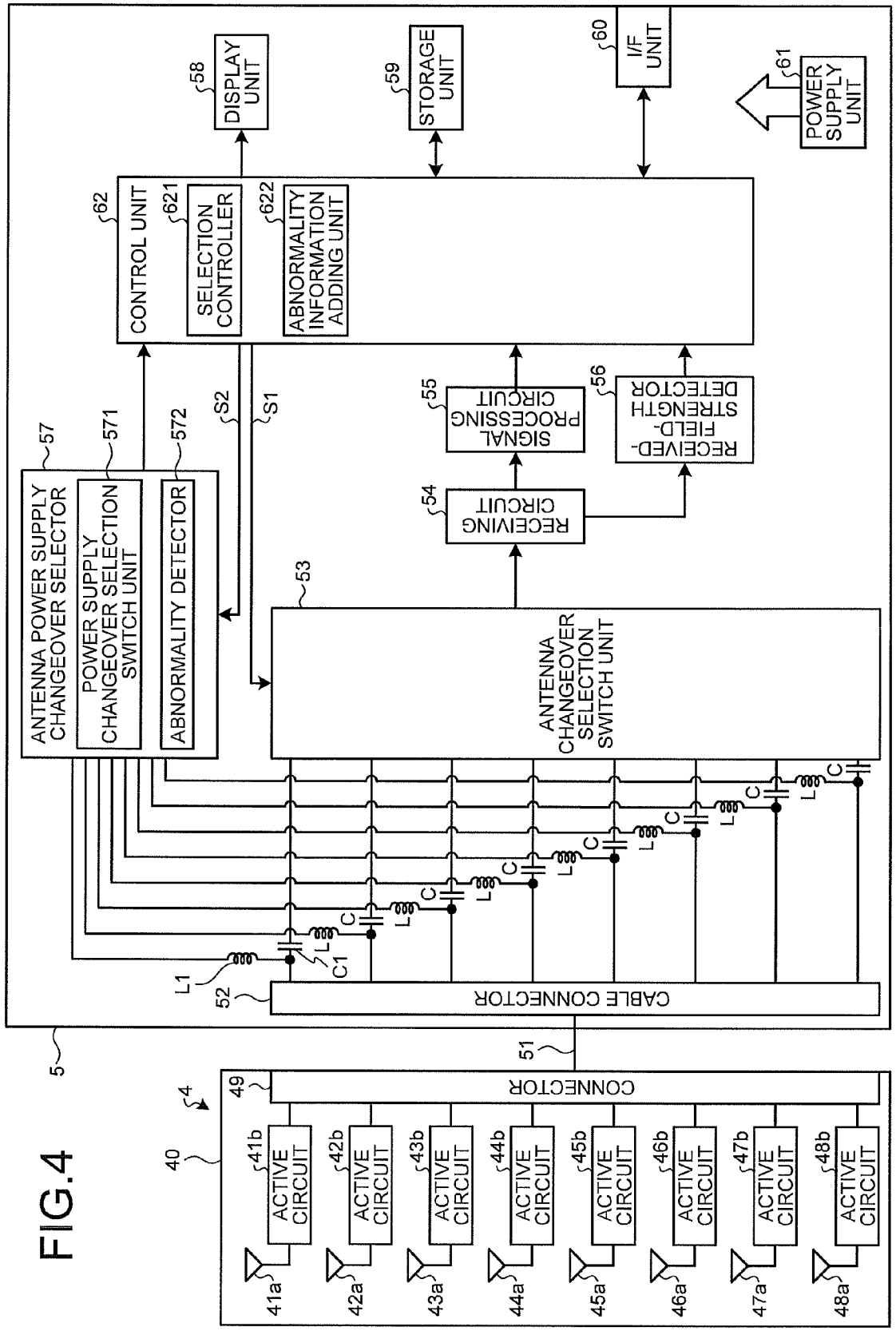
FIG. 4 is a block diagram that illustrates a schematic configuration of a receiving apparatus illustrated in FIG. 1.

Next, details of the configuration of the receiving apparatus illustrated in FIG. 1 are described. FIG. 4 is a block diagram that illustrates the configuration of the receiving apparatus illustrated in FIG. 1. In the following description, when any one of the first to eighth receiving antennas 41 to 48 is described, the first receiving antenna 41 (the element 41a, the active circuit 41b) is representatively described.

As illustrated in FIG. 4, the receiving apparatus 5 includes the antenna cable 51 connected to each of the first to eighth receiving antennas 41 to 48 via the connector 49 of the antenna apparatus 4, a cable connector 52 to which the antenna cable 51 is connected, an antenna changeover selection switch unit 53 that selectively switches among the first to eighth receiving antennas 41 to 48, a receiving circuit 54 that performs processing such as modulation on a radio signal received through any one of the first to eighth receiving antennas 41 to 48 which is selected by the antenna changeover selection switch unit 53, a signal processing circuit 55 that performs signal processing of extracting image data and the like from the radio signal output from the receiving circuit 54, a received-field-strength detector 56 that detects a received field strength based on the strength of the radio signal output from the receiving circuit 54, an antenna power supply changeover selector 57 that switches among the first to eighth receiving antennas 41 to 48 and supplies power to any one of the first to eighth receiving antennas 41 to 48, a display unit 58 that displays an image corresponding to the image data received from the capsule endoscope 3, a storage unit 59 that stores various information including the image data received from the capsule endoscope 3, an I/F unit 60 that mutually transmits and receives data to and from the image display apparatus 6 via the cradle 6a, a power supply unit 61 that supplies power to all the units of the receiving apparatus, and a control unit 62 that controls the operation of the receiving apparatus 5.

The antenna cable 51 is configured by a coaxial cable. The antenna cable 51 has core wires, the number of which corresponds to the number of the first to eighth receiving antennas 41 to 48. For example, the antenna cable 51 has eight core wires. The antenna cable 51 transmits the radio signals received by each of the first to eighth receiving antennas 41 to 48 to the receiving apparatus 5, and transmits the power supplied from the receiving apparatus 5 to each of the first to eighth receiving antennas 41 to 48.

The antenna cable 51 is connected to the cable connector 52 in a detachable manner. The cable connector 52 is electrically connected to the antenna changeover selection switch unit 53 and the antenna power supply changeover selector 57.

The antenna changeover selection switch unit 53 is configured by a mechanical switch, a semiconductor switch, or the like. The antenna changeover selection switch unit 53 is electrically connected to each of the first to eighth receiving antennas 41 to 48 via a capacitor C1. When a switch signal S1 used to switch the receiving antenna which receives the radio signal is input from the control unit 62, the antenna changeover selection switch unit 53, for example, selects the first receiving antenna 41 as instructed by the switch signal S1 and outputs the received radio signal through the selected first receiving antenna 41 to the receiving circuit 54. The capacitance of each of capacitors respectively connected to the first to eighth receiving antennas 41 to 48 is equal to the capacitance of the capacitor C1.

The receiving circuit 54 performs predetermined processing such as demodulation or amplification on the radio signal received through the first receiving antenna 41 selected by the antenna changeover selection switch unit 53, and outputs the processed signal to each of the signal processing circuit 55 and the received-field-strength detector 56.

The signal processing circuit 55 extracts the image data from the radio signal input from the receiving circuit 54, performs predetermined processing, for example, various kinds of image processing and/or A/D conversion processing on the extracted image data, and outputs the resultant signal to the control unit 62.

The received-field-strength detector 56 detects the received field strength corresponding to the strength of the radio signal input from the receiving circuit 54, and outputs a received-field-strength signal (RSSI: Received Signal Strength Indicator) corresponding to the detected received field strength to the control unit 62.

The antenna power supply changeover selector 57 is electrically connected to each of the first to eighth receiving antennas 41 to 48 via a coil L1. The antenna power supply changeover selector 57 supplies the power to the first receiving antenna 41 selected by the antenna changeover selection switch unit 53 through the antenna cable 51. The antenna power supply changeover selector 57 includes a power supply changeover selection switch unit 571 and an abnormality detector 572. The electrical characteristic of each of coils respectively connected to the first to eighth receiving antennas 41 to 48 is equal to the characteristic of the coil L1.

The power supply changeover selection switch unit 571 is configured by a mechanical switch, a semiconductor switch, or the like. When a selection signal S2 used to select the receiving antenna which is to be supplied with power is input from the control unit 62, the power supply changeover selection switch unit 571 selects, for example, the first receiving antenna 41 as instructed by the selection signal S2, and supplies power only to the selected first receiving antenna 41.

The abnormality detector 572 outputs, to the control unit 62, an abnormality signal indicating an event that abnormality is caused in the first receiving antenna 41 to which power is supplied, when abnormality occurs in the first receiving antenna 41 to which power is supplied. Specifically, the abnormality detector 572 detects a disconnection abnormality or a short-circuit abnormality in the first receiving antenna 41 based on the voltage supplied to the first receiving antenna 41 selected by the power supply changeover selection switch unit 571, and outputs the detection result to the control unit 62.

The display unit 58 is configured by using a display panel composed of liquid crystal, organic Electro Luminescence (EL), or the like. The display unit 58 displays various information such as images corresponding to the image data captured by the capsule endoscope 3, operation status of the receiving apparatus 5, patient information of the subject 2, and examination data and time.

The storage unit 59 is configured by a semiconductor memory such as flash memory and Random Access Memory (RAM) provided fixedly in the receiving apparatus 5. The storage unit 59 stores the image data captured by the capsule endoscope 3 and/or various kinds of information associated with the image data, for example, position information of the capsule endoscope 3, orientation information of the capsule endoscope 3, received-field-strength information, and identification information used to identify the receiving antenna that has received the radio signal. The storage unit 59 stores various kinds of programs to be executed by the receiving apparatus 5. The storage unit 59 may have a function as a recording medium interface which stores information in an external recording medium such as a memory card, and reads information stored in the recording medium.

The I/F unit 60 functions as a communication interface and mutually transmits and receives data to and from the image display apparatus 6 through the cradle 6a.

The power supply unit 61 is configured by a battery detachable from the receiving apparatus 5 and a switch unit which performs switching between ON state and OFF state. The power supply unit 61 supplies necessary driving power to each unit of the receiving apparatus 5 when it is in ON state, and stops supplying the driving power to each unit of the receiving apparatus 5 when it is in OFF state.

The control unit 62 is configured by a Central Processing Unit (CPU) or the like. The control unit 62 reads the programs out of the storage unit 59 and executes the programs, and collectively controls the operation of the receiving apparatus 5 by giving instructions or transmitting data to the respective units which constitute the receiving apparatus 5. The control unit 62 includes a selection controller 621 and an abnormality information adding unit 622.

The selection controller 621 performs control of selecting the receiving antenna to receive the radio signal transmitted from the capsule endoscope 3 and supplying power only to the selected receiving antenna. Specifically, the selection controller 621 performs control of selecting the receiving antenna to receive the radio signal transmitted from the capsule endoscope 3 and supplying power only to the selected receiving antenna, based on the received electric field strengths of the first to eighth receiving antennas 41 to 48 which are detected by the received-field-strength detector 56. For example, the selection controller 621 drives the antenna changeover selection switch unit 53 at every predetermined timing, for example, every 100 msec to sequentially select the receiving antennas to receive the radio signal transmitted from any one of the first to eighth receiving antennas 41 to 48, and repeats such a process until the received electric field strength detected by the received-field-strength detector 56 reaches a predetermined value.

When the abnormality detector 572 detects abnormality caused in any one of the first to eighth receiving antennas 41 to 48, the abnormality information adding unit 622 adds abnormality information indicating that abnormality is caused in any one of the first to eighth receiving antennas 41 to 48 to the radio signals which are respectively received by the first to eighth receiving antennas 41 to 48, and outputs the resultant signal to the storage unit 59. Specifically, the abnormality information adding unit 622 adds a flag indicating the abnormality information to the image data which has been subjected to the signal processing performed by the signal processing circuit 55, for each of the radio signals respectively received by the first to eighth receiving antennas 41 to 48, and outputs the resultant signal to the storage unit 59.

Antenna switch and selection processing performed by the selection controller 621 in the antenna apparatus 4 and the receiving apparatus 5 configured in this way is described below.

First, along with the activation of the receiving apparatus 5, the selection controller 621 performs control of selecting any one of the first to eighth receiving antennas 41 to 48 by activating the antenna changeover selection switch unit 53 at every predetermined timing, for example, every 100 msec and supplying power only to the receiving antenna selected by the antenna changeover selection switch unit 53. In this case, the abnormality detector 572 detects each of the disconnection abnormality and the short-circuit abnormality in each of the first to eighth receiving antennas 41 to 48 sequentially selected by the selection controller 621, and outputs the detection result to the control unit 62. The control unit 62 determines whether abnormality is caused in any one of the first to eighth receiving antennas 41 to 48 based on the detection result of the abnormality detector 572. The control unit 62 may output the detection result with respect to the first to eighth receiving antennas 41 to 48 to the display unit 58. In this way, the user can check whether there is abnormality caused in any one of the first to eighth receiving antennas 41 to 48. As a result, it is possible to prevent the examination result of the subject 2 from becoming useless, which may occur because it is difficult to acquire highly precise and accurate image data due to the abnormality of the receiving antenna.

After pre-processing performed along with the activation of the receiving apparatus 5, the capsule endoscope 3 is introduced into the subject 2. Along with the introduction, the selection controller 621 performs control of sequentially switching and selecting the receiving antenna to receive the radio signal transmitted from the capsule endoscope 3 at every predetermined timing and supplying power only to the selected receiving antenna.

Next, the selection controller 621 selects the receiving antenna where the received electric field strength detected by the received-field-strength detector 56 is strongest among the first to eighth receiving antennas 41 to 48, and supplies power only to the selected receiving antenna.

After that, the selection controller 621 performs control of switching among the first to eighth receiving antennas 41 to 48 to select one receiving antenna to receive the radio signal transmitted from the capsule endoscope 3 at every predetermined timing until the capsule endoscope 3 is excreted from the inside of the subject 2, and supplying power only to the selected receiving antenna. In this case, the abnormality detector 572 detects each of the disconnection abnormality and the short-circuit abnormality caused in one of the first to eighth receiving antennas 41 to 48 selected by the selection controller 621, and outputs the detection result to the control unit 62. The control unit 62 determines whether abnormality is caused in any of the first to eighth receiving antennas 41 to 48 based on the detection result of the abnormality detector 572.

When abnormality is caused in any one of the first to eighth receiving antennas 41 to 48, the abnormality information adding unit 622 adds abnormality information indicating that abnormality is caused in any of the first to eighth receiving antennas 41 to 48 to the image data, which has been received by any one of the first to eighth receiving antennas 41 to 48 and has been subjected to the signal processing performed by the signal processing circuit 55, and stores the resultant in the storage unit 59. As a result, when the image of the inside of the subject 2 captured by the capsule endoscope 3 is displayed by the image display apparatus 6, the image display apparatus 6 displays the abnormal information added to the image data. Accordingly, it is possible to determine whether abnormality was caused in the first to eighth receiving antennas 41 to 48 at certain time points, which enables to determine whether the image data can be used for inspection.

According to the embodiment of the present invention described above, the antenna apparatus includes the first receiving antenna 41 and the second receiving antenna 42 disposed at positions on a plane, which face each other with the reference point $O_1$ therebetween and are in an equal distance from the reference point $O_1$, the third receiving antenna 43 and the fourth receiving antenna 44 disposed at positions which are in-plane rotated about the reference point $O_1$ by 90 degrees from the first receiving antenna 41 and the second receiving antenna 42, respectively, the fifth receiving antenna 45 and the sixth receiving antenna 46 disposed at positions which are closer to outer peripheries of the plane than the first receiving antenna 41 and the second receiving antenna 42 and which are in-plane rotated about the reference point $O_1$ by 45 degrees from the first receiving antenna 41 and the second receiving antenna 42, respectively, and the seventh receiving antenna 47 and the eighth receiving antenna 48 disposed at positions which are in-plane rotated about the reference point $O_1$ by 90 degrees from the fifth receiving antenna 45 and the sixth receiving antenna 46, respectively. As a result, the radio signal transmitted from the capsule endoscope 3 introduced in the subject 2 is precisely detected and the position of the capsule endoscope 3 can be accurately detected.

Furthermore, according to the embodiment of the present invention, the selection controller 621 performs control of selecting one receiving antenna to receive the radio signal transmitted from the outside from among the first to eighth receiving antennas 41 to 48 and supplying power only to the selected receiving antenna. As a result, even when a plurality of active antennas, each being provided with an active circuit, is used, power consumption may be reduced and influence of the interference among the receiving antennas also may be reduced.

Furthermore, according to the embodiment of the present invention, the abnormality detector 572 detects each of the disconnection abnormality and the short-circuit abnormality and outputs the detection result to the control unit 62. As a result, the control unit 62 can easily determine whether there is abnormality caused in any one of the first to eighth receiving antennas 41 to 48 at the time of activation of the capsule endoscope 3 and the receiving apparatus 5, or during the examination of the subject 2.

Moreover, according to the embodiment of the present invention, the antenna cable which connects the antenna apparatus 4 and the receiving apparatus 5 can be integrated in one cable, resulting in a reduction in the failure of the antenna cable.

Moreover, according to the embodiment of the present invention, since the first to eighth receiving antennas 41 to 48 are provided with the active circuits 41b to 48b, respectively, the radio signal transmitted from the capsule endoscope 3 can be received without having to closely attach the first to eighth receiving antennas 41 to 48 to the subject 2.

Yet furthermore, according to the embodiment of the present invention, when radiation pattern of the radio signal transmitted by the capsule endoscope 3 and the shape of a transmitting antenna of the capsule endoscope 3 which transmits the radio signal in a polarization direction are known beforehand, the received field strength is measured by all the first to eighth receiving antennas 41 to 48, and the position and direction of the capsule endoscope 3 are detected while taking balance among the received field strengths of the first to eighth receiving antennas 41 to 48. With this method, the position of the capsule endoscope 3 in the subject 2 can be easily estimated.

According to the embodiment of the present invention, the capsule endoscope 3 modulates the image data acquired from the subject 2 and transmits the result as the radio signal. Thus, by receiving and demodulating the radio signal using the receiving antenna with the strongest received field strength among the first to eighth receiving antennas 41 to 48, the image data can be reliably restored.

In the embodiment of the present invention, the third receiving antenna 43 and the fourth receiving antenna 44 are disposed at positions which are in-plane rotated about the reference point $O_1$ by 90 degrees from the first receiving antenna 41 and the second receiving antenna 42, respectively, the fifth receiving antenna 45 and the sixth receiving antenna 46 are disposed at positions which are in-plane rotated about the reference point $O_1$ by 45 degrees from the first receiving antenna 41 and the second receiving antenna 42, respectively, and the seventh receiving antenna 47 and the eighth receiving antenna 48 are disposed at positions which are in-plane rotated about the reference point $O_1$ by 90 degrees from the fifth receiving antenna 45 and the sixth receiving antenna 46, respectively. However, the positions to arrange the fifth to eighth receiving antennas 45 to 48 may be changed. Specifically, the third receiving antenna 43 and the fourth receiving antenna 44 may be disposed at such positions on the plate unit 40 that the gravity center of the third receiving antenna 43 and the gravity center of the fourth receiving antenna 44 are in an equal distance from the reference point $O_1$ and a straight line which connects the gravity center of the third receiving antenna 43 and the gravity center of the fourth receiving antenna 44 is at an angle of 90 degrees with respect to a straight line which connects the gravity center of the first receiving antenna 41 and the gravity center of the second receiving antenna 42. Moreover, the fifth receiving antenna 45 and the eighth receiving antenna 48 may be disposed at such positions on the plate unit 40 that the gravity center of the fifth receiving antenna 45 and the gravity center of the eighth receiving antenna 48 are arranged in straight lines, respectively, which are different from each other and each of which is at an angle of 45 degrees with respect to both a straight line which connects the gravity center of the first receiving antenna 41 and the gravity center of the second receiving antenna 42 and a straight line which connects the gravity center of the third receiving antenna 43 and the gravity center of the fourth receiving antenna 44.

Modification 1

Figure 5:
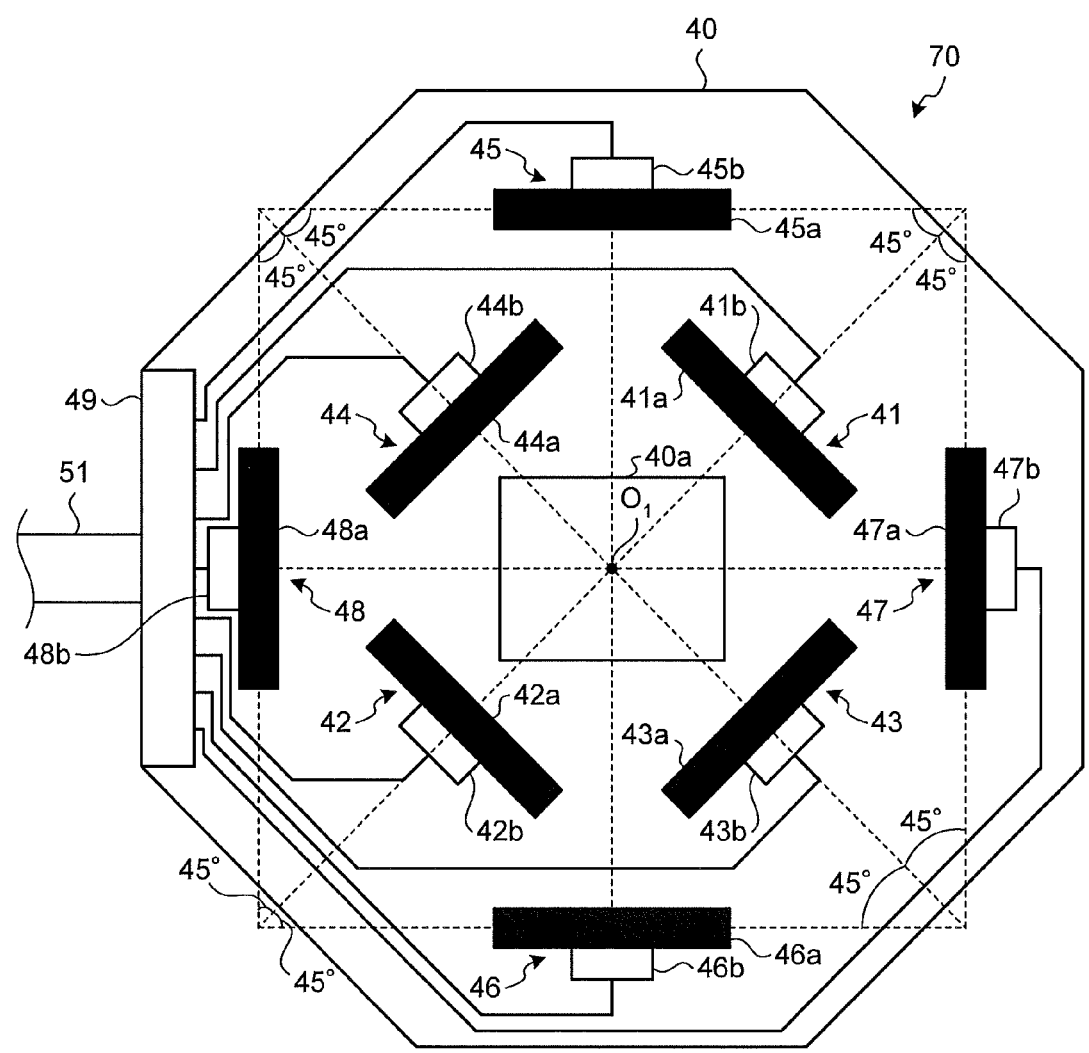
FIG. 5 is a plan view that illustrates a schematic configuration of an antenna apparatus according to Modification 1 of the embodiment of the present invention.

In the embodiment described above, the positions at which the first to eighth receiving antennas 41 to 48 are arranged may be changed. FIG. 5 is a plan view that illustrates a schematic configuration of an antenna apparatus according to Modification 1 of the embodiment of the present invention. As illustrated in FIG. 5, in an antenna apparatus 70, first to eighth receiving antennas 41 to 48 are disposed at positions which are rotated about the reference point $O_1$ by 45 degrees respectively from the arrangement positions in the above described embodiment. With this configuration, the same effects as the above-described embodiment can be achieved.

Modification 2

Figure 6:
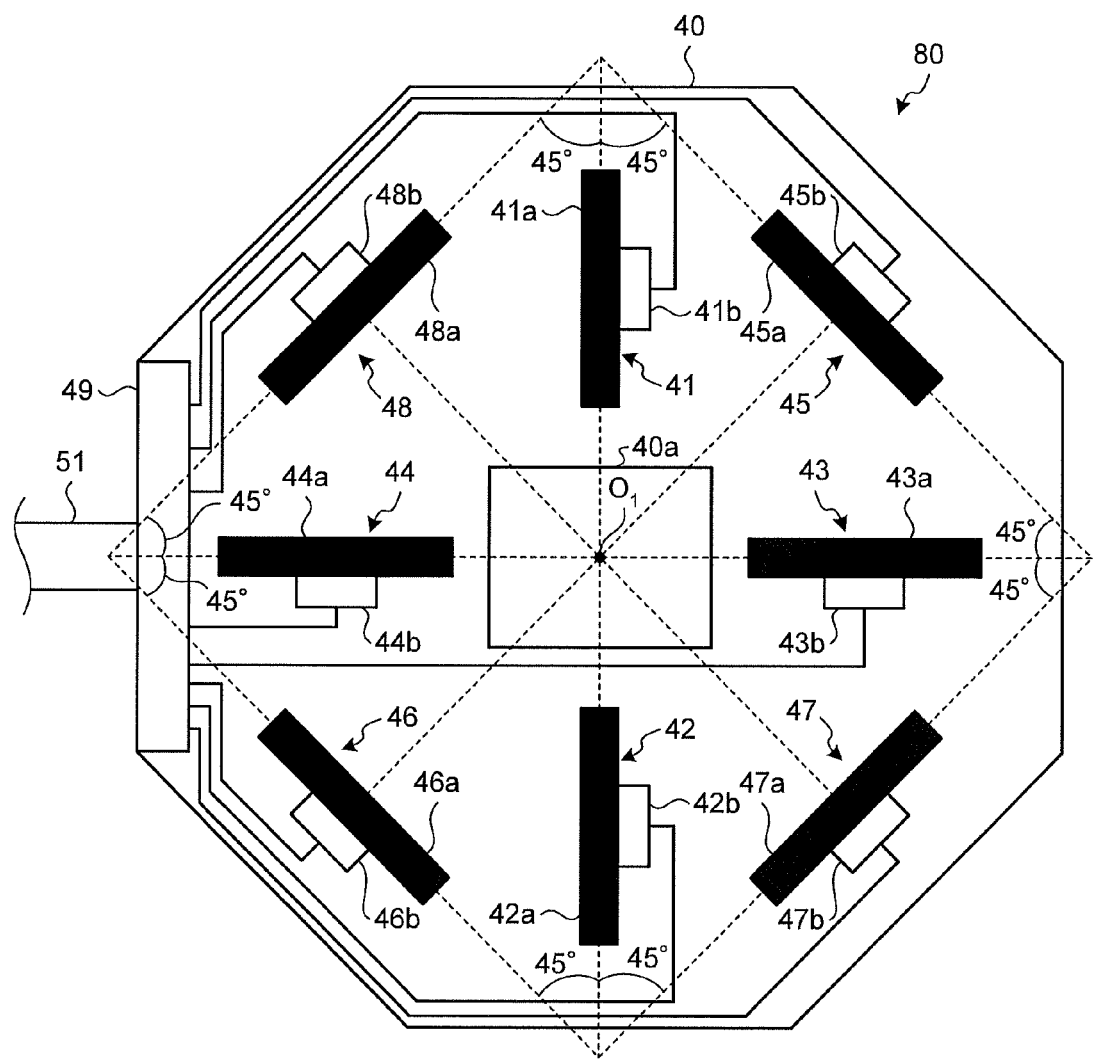
FIG. 6 is a plan view that illustrates a schematic configuration of an antenna apparatus according to Modification 2 of the embodiment of the present invention.

FIG. 6 is a plan view that illustrates a schematic configuration of an antenna apparatus according to Modification 2 of the embodiment of the present invention. As illustrated in FIG. 6, in an antenna apparatus 80, an element 41a of a first receiving antenna 41 and an element 42a of a second receiving antenna 42 are arranged to face each other with a reference point $O_1$ therebetween on a straight line passing the reference point $O_1$. Moreover, in the antenna apparatus 80, an element 43a of a third receiving antenna 43 and an element 44a of a fourth receiving antenna 44 are arranged to face each other with the reference point $O_1$ therebetween on a straight line passing the reference point $O_1$. With this configuration, the same effects as the above-described embodiment can be achieved.

Modification 3

Figure 7:
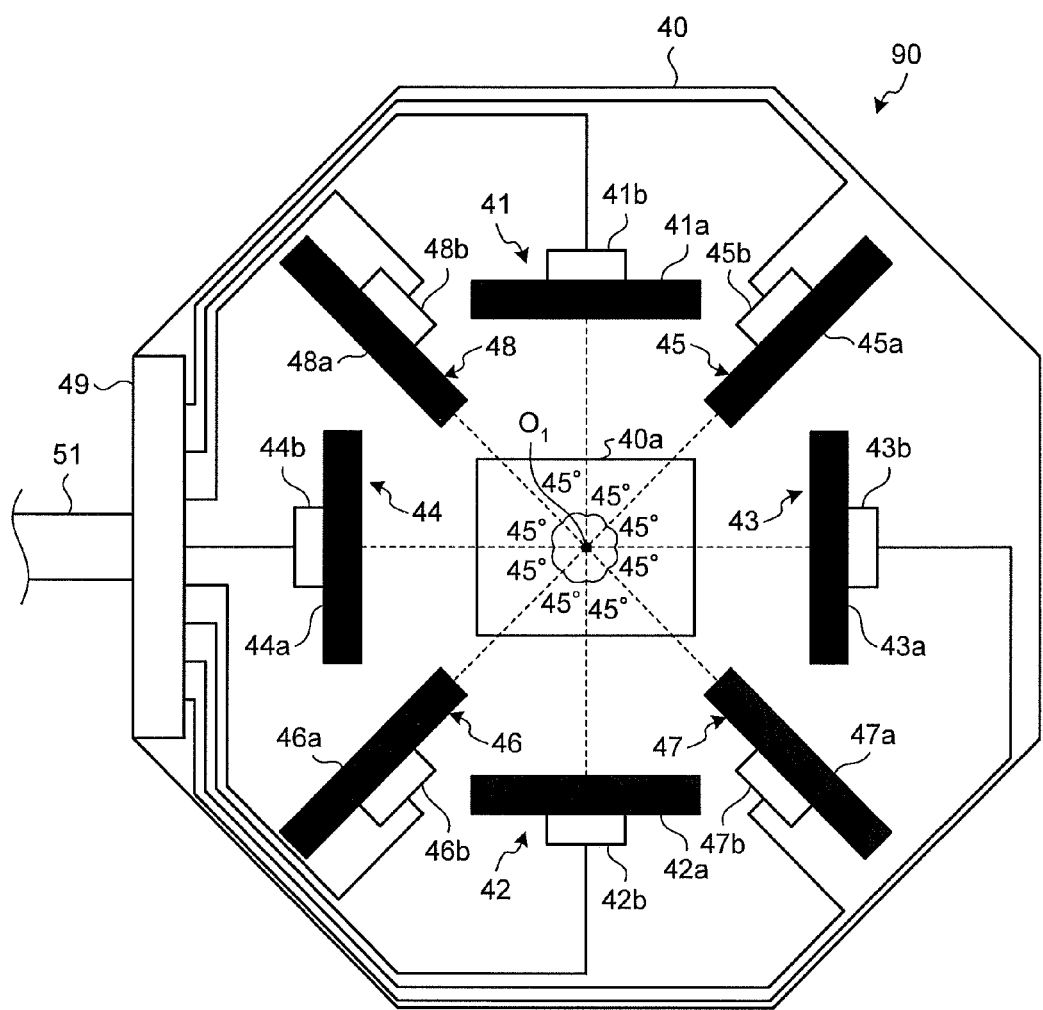
FIG. 7 is a plan view that illustrates a schematic configuration of an antenna apparatus according to Modification 3 of the embodiment of the present invention.

FIG. 7 is a plan view that illustrates a schematic configuration of an antenna apparatus according to Modification 3 of the embodiment of the present invention. As illustrated in FIG. 7, in an antenna apparatus 90, an element 45a of a fifth receiving antenna 45 and an element 46a of a sixth receiving antenna 46 are arranged to face each other with a reference point $O_1$ therebetween in a straight line passing the reference point $O_1$. Moreover, in the antenna apparatus 90, an element 47a of a seventh receiving antenna 47 and an element 48a of an eighth receiving antenna 48 are arranged to face each other with a reference point $O_1$ therebetween in a straight line passing the reference point $O_1$. With this configuration, the same effects as the above-described embodiment can be achieved.

Modification 4

Figure 8:
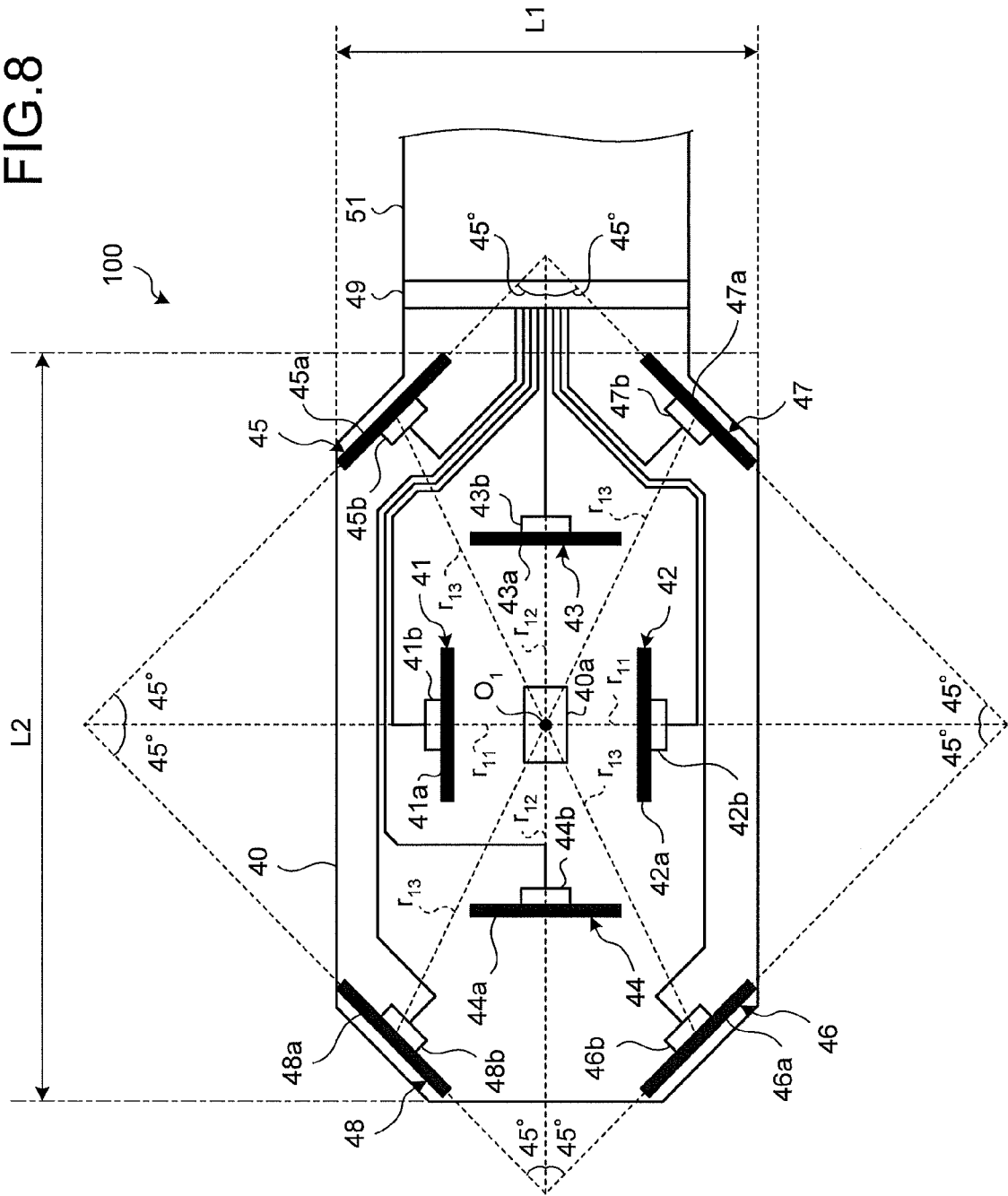
FIG. 8 is a plan view that illustrates a schematic configuration of an antenna apparatus according to Modification 4 of the embodiment of the present invention.

FIG. 8 is a plan view that illustrates a schematic configuration of an antenna apparatus according to Modification 4 of the embodiment of the present invention.

As illustrated in FIG. 8, an antenna apparatus 100 includes: a first receiving antenna 41 and a second receiving antenna 42 disposed at positions on a plane, which face each other with a reference point $O_1$ therebetween and are in a distance of r11 from the reference point $O_1$; a third receiving antenna 43 and a fourth receiving antenna 44 disposed at positions which are in-plane rotated about the reference point $O_1$ by 90 degrees from a straight line which connects the gravity center of the first receiving antenna 41 and the gravity center of the second receiving antenna 42; a fifth receiving antenna 45 and a sixth receiving antenna 46 disposed at positions which are closer to outer peripheries of the plane than the first receiving antenna 41 and the second receiving antenna 42, an extending direction of each of the fifth and sixth receiving antennas 45 and 46 being a straight line having an angle of 45 degrees with respect to a straight line which connects the gravity center of the first receiving antenna 41 and the gravity center of the second receiving antenna 42, the gravity centers of the fifth and sixth receiving antennas 45 and 46 being disposed at positions within the plane; and a seventh receiving antenna 47 and an eighth receiving antenna 48 disposed at positions closer to the outer peripheries of the plane than the third receiving antenna 43 and the fourth receiving antenna 44, an extending direction of the seventh receiving antenna 47 and the eighth receiving antenna 48 being a straight line having an angle of 45 degrees with respect to a straight line which connects the gravity center of the third receiving antenna 43 and the gravity center of the fourth receiving antenna 44, the gravity centers of the seventh receiving antenna 47 and the eighth receiving antenna 48 being disposed at positions within the plane.

Specifically, the third receiving antenna 43 and the fourth receiving antenna 44 are disposed respectively at positions on a plate unit 40 which are in an equal distance of $r_{12}$ ($r_{11} < r_{12}$) from the reference point $O_1$, and are more away from each other than those of the first receiving antenna 41 and the second receiving antenna 42. Moreover, the fifth to eighth receiving antennas 45 to 48 are disposed respectively at positions on the plate unit 40 which are in an equal distance of $r_{13}$ ($r_{12} < r_{13}$) from the reference point, and are more away from each other than those of the third receiving antenna 43 and the fourth receiving antenna 44. With this configuration, the plate unit 40 of the receiving antenna apparatus 100 may be decreased in length L1 and increased in width L2.

According to Modification 4 of the embodiment described above, the same effect as the above-described embodiment can be achieved, and the antenna apparatus 100 can be easily attached to the subject 2.

According to Modification 4 of the embodiment of the present invention described above, both of the third receiving antenna 43 and the fourth receiving antenna 44 may be arranged on the outer periphery of the plate unit 40.

Modification 5

Figure 9:
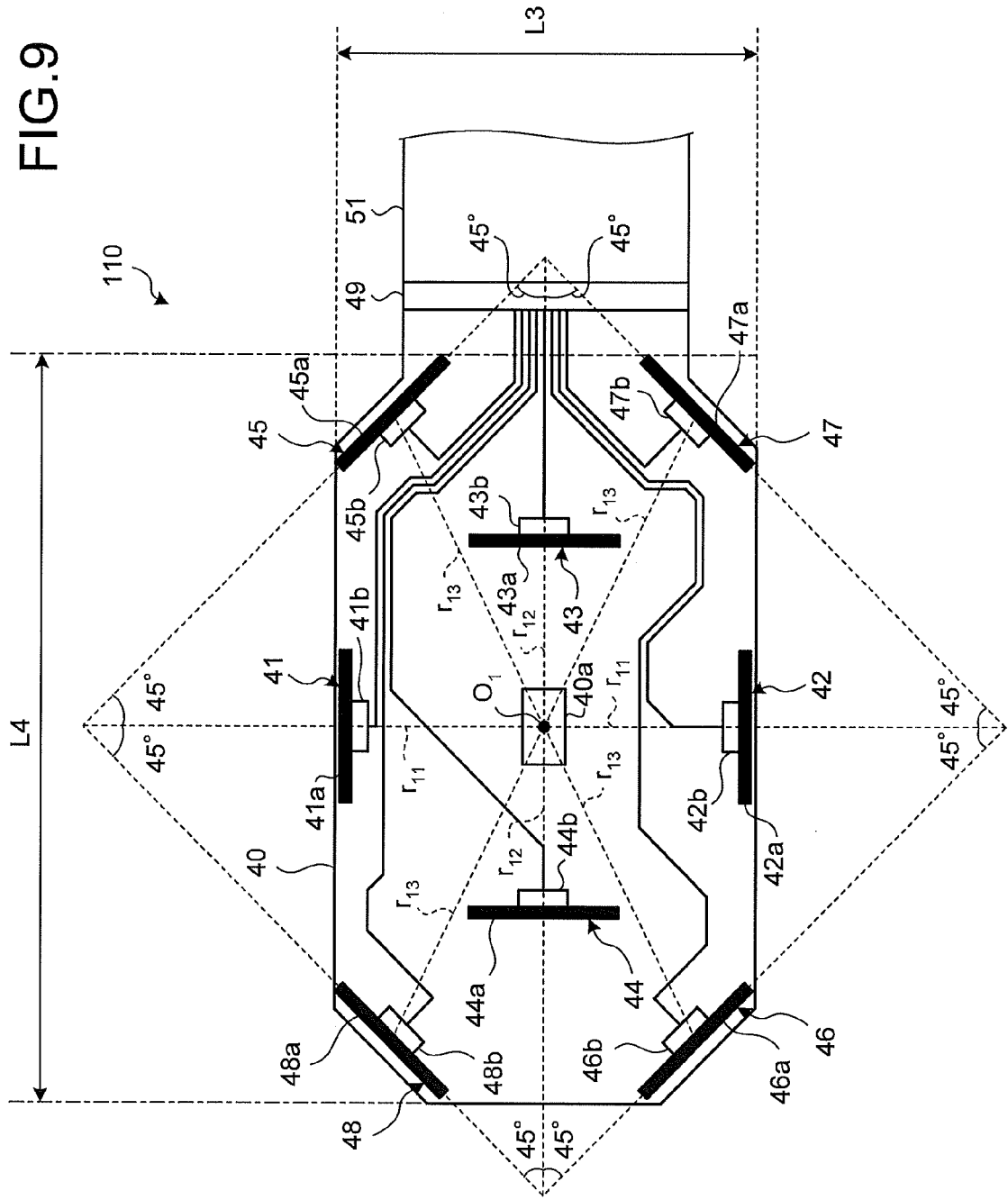
FIG. 9 is a plan view that illustrates a schematic configuration of an antenna apparatus according to Modification 5 of the embodiment of the present invention.

In Modification 4 of the embodiment described above, the distance between the first receiving antenna 41 and the second receiving antenna 42 and the distance between the third receiving antenna 43 and the fourth receiving antenna 44 may be changed. FIG. 9 is a plan view that illustrates a schematic configuration of an antenna apparatus according to Modification 5 of the embodiment of the present invention. Hereinbelow, the first receiving antenna 41 and the second receiving antenna 42 are described as the third receiving antenna 43 and the fourth receiving antenna 44, and the third receiving antenna 43 and the fourth receiving antenna 44 are described as the first receiving antenna 41 and the second receiving antenna 42.

As illustrated in FIG. 9, in a receiving antenna 110, a first receiving antenna 41 and a second receiving antenna 42 are disposed respectively at positions on a plate unit 40 which are in an equal distance of $r_{11}$ ($r_{12} < r_{11}$) from a reference point $O_1$, are more away from each other than those of a third receiving antenna 43 and a fourth receiving antenna 44, and are closer to outer peripheries of the plate unit 40. Specifically, the first receiving antenna 41 and the second receiving antenna 42 are disposed such that an element 41a and an element 42a thereof are both formed on the outer periphery of the plate unit 40. Moreover, the fifth to eighth receiving antennas 45 to 48 are disposed respectively at positions on the plate unit 40 which are in an equal distance of $r_{13}$ ($r_{12} < r_{13}$) from the reference point $O_1$, and are more away from each other than those of the third receiving antenna 43 and the fourth receiving antenna 44. With this configuration, the receiving antenna 110 can be configured such that the length L3 of the plate unit 40 is further reduced compared with the length L1 of Modification 4 of the embodiment described above (L1>L3) and the width L4 of the plate unit 40 is increased. For example, as for a receiving apparatus, the plate unit 40 thereof may have a length L3 of 140 mm and a width L4 of 190 mm.

According to Modification 5 of the embodiment described above, the same effect as the above-described embodiment can be achieved, and the length of the plate unit 40 can be reduced, so that the antenna apparatus 110 can be easily attached to the subject 2.

In Modification 5 of the embodiment of the present invention described above, the first receiving antenna 41 and the second receiving antenna 42 may be disposed on the outer peripheries of the plate unit 40, respectively.

Other Embodiments

In the embodiment described above, although the active circuits are connected to the first to eighth receiving antennas 41 to 48, respectively, transformation circuits (balun) which transform balanced state to unbalanced state may be connected to the first to eighth receiving antennas 41 to 48, respectively.

Moreover, although the first to eighth receiving antennas 41 to 48 are configured by dipole antennas in the embodiment described above, the first to eighth receiving antennas 41 to 48 may be configured by loop antennas or open type antennas.

Furthermore, although the abnormality detector 572 detects the abnormality of the first to eighth receiving antennas 41 to 48 based on voltage in the embodiment described above, the abnormality of the first to eighth receiving antennas 41 to 48 may be detected based on current and/or power. Yet furthermore, the abnormality detector 572 may detect the abnormality of the first to eighth receiving antennas 41 to 48 based on a combination of voltage, current, and power.

In the embodiment described above, the image display apparatus 6 can acquire in-vivo image data captured by the capsule endoscope 3 in various ways. For example, in the receiving apparatus 5, a memory card such as a USB memory and a compact flash (registered trademark) which can be removed from the receiving apparatus 5 may be used instead of the built-in storage unit 59. In this case, after the image data is loaded from the capsule endoscope 3 to the memory, only the memory is removed from the receiving apparatus 5, and then the memory may be inserted into a USB port or the like of the image display apparatus 6 for example. Furthermore, the image display apparatus 6 may be provided with a communication function, so that the image data may be acquired from the receiving apparatus 5 by wired communication or wireless communication.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An antenna apparatus comprising:
    a first receiving antenna and a second receiving antenna respectively disposed at positions on a plane which are in an equal distance from a reference point and face each other with the reference point therebetween;
    a third receiving antenna and a fourth receiving antenna disposed at positions on the plane, a gravity center of the third receiving antenna and a gravity center of the fourth receiving antenna being in an equal distance from the reference point on the plane, a straight line connecting the gravity centers of the third receiving antenna and the fourth receiving antenna being at an angle of 90 degrees with respect to a straight line connecting a gravity center of the first receiving antenna and a gravity center of the second receiving antenna;
    a fifth receiving antenna, a sixth receiving antenna, a seventh receiving antenna, and an eighth receiving antenna disposed respectively at positions on the plane, gravity centers of the fifth to eighth receiving antennas being on straight lines different from each other, which are rotated by an angle of 45 degrees from the straight line connecting the gravity centers of the first receiving antenna and the second receiving antenna and the straight line connecting the gravity centers of the third receiving antenna and the gravity center of the fourth receiving antenna, respectively,
    wherein each of the first to the eighth receiving antennas is formed such that two conductive wires symmetrically extend to left and right sides to be in a straight line and have a same length,
    a direction of the conductive wires of the first receiving antenna is parallel to a direction of the conductive wires of the second receiving antenna, a direction of the conductive wires of the third receiving antenna is parallel to a direction of the conductive wires of the fourth receiving antenna and orthogonal to the direction of the conductive wires of the first receiving antenna and the direction of the conductive wires of the second receiving antenna, a direction of the conductive wires of the fifth receiving antenna is parallel to a direction of the conductive wires of the sixth receiving antenna, and a direction of the conductive wires of the seventh receiving antenna is parallel to a direction of the conductive wires of the eighth receiving antenna and orthogonal to the direction of the conductive wires of the fifth receiving antenna and the direction of the conductive wires of the sixth receiving antenna.

2. The antenna apparatus according to claim 1, wherein the first to fourth receiving antennas are disposed respectively at positions which are in an equal distance from the reference point within the plane.

3. The antenna apparatus according to claim 1, wherein the third and fourth receiving antennas are in an equal distance from the reference point and are disposed, with respect to the reference point, closer to outer peripheries of the plane than the first and second receiving antennas.

4. The antenna apparatus according to claim 1, wherein the first to eighth receiving antennas are balanced antennas exhibiting a larger loss in cross polarization than in main polarization.

5. The antenna apparatus according to claim 1, wherein the first to eighth receiving antennas are dipole antennas.

6. The antenna apparatus according to claim 1, wherein the first to eighth receiving antennas are provided with first to eighth active circuits, respectively.

7. The antenna apparatus according to claim 1, wherein the first to eighth receiving antennas are disposed on one plate unit.

8. The antenna apparatus according to claim 7, wherein the third and fourth receiving antennas are disposed on outer peripheries of the plate unit.

9. The antenna apparatus according to claim 8, further comprising:

first to eighth transmission lines to transmit and receive a signal to and from the first to eighth receiving antennas, respectively, and wherein the first to eighth transmission lines gather at an end portion of the plate unit.

10. The antenna apparatus according to claim 7, wherein the plate unit includes a positioning unit that positions the antenna apparatus with respect to a target object to which the antenna apparatus is mounted.

* * * * *